United States Patent
Kawaji et al.

(10) Patent No.: US 9,702,956 B2
(45) Date of Patent: Jul. 11, 2017

(54) MRI METHODS AND APPARATUS FOR FLEXIBLE VISUALIZATION OF ANY SUBSET OF AN ENLARGED TEMPORAL WINDOW

(71) Applicant: Beth Israel Deaconess Medical Center, Inc. (BIDMC, Inc.), Boston, MA (US)

(72) Inventors: Keigo Kawaji, Chicago, IL (US); Reza Nezafat, Newton, MA (US); Warren J Manning, Natick, MA (US)

(73) Assignee: Beth Israel Deaconess Medical Center, Inc. (BIDMC, INC.), Boston, MA (US)

( * ) Notice: Subject to any disclaimer, the term of this patent is extended or adjusted under 35 U.S.C. 154(b) by 188 days.

(21) Appl. No.: 14/274,065

(22) Filed: May 9, 2014

(65) Prior Publication Data
US 2015/0276909 A1  Oct. 1, 2015

Related U.S. Application Data

(60) Provisional application No. 61/970,059, filed on Mar. 25, 2014.

(51) Int. Cl.
*A61B 5/055* (2006.01)
*G01R 33/567* (2006.01)
(Continued)

(52) U.S. Cl.
CPC .......... *G01R 33/5673* (2013.01); *A61B 5/024* (2013.01); *A61B 5/055* (2013.01);
(Continued)

(58) Field of Classification Search
CPC ....... A61B 5/055; A61B 5/411; A61B 5/7285; A61B 5/0037; G01R 33/563; G01R 33/4822; G01R 33/5676
See application file for complete search history.

(56) References Cited

U.S. PATENT DOCUMENTS 6,198,959 B1 * 3/2001 Wang .................... A61B 5/055
324/307

FOREIGN PATENT DOCUMENTS

JP    2013-521955 A    6/2013
KR   10-2004-0071643 A   8/2004
(Continued)

OTHER PUBLICATIONS

Korean Notice of Allowance dated Apr. 20, 2016.

*Primary Examiner* — Elmer Chao
(74) *Attorney, Agent, or Firm* — Cha & Reiter, LLC

(57) ABSTRACT

A method and apparatus for MRI retrospective reconstruction determines a period of minimal coronary artery motion within the acquired temporal window with a rotation angle optimized for a K-space four-dimensional (4D) volume by a segmented 4D radial stack-of-stars (SOS) acquisition during a temporal acquisition window (taw). Radial stacks of the image of an object are acquired by performing the radial (SOS) acquisition to determine a plurality of $k_z$ plane samples of the object, in which each $k_z$ plane is repeatedly determined during a sub-window of the temporal acquisition window. Consecutive volumes of $k_z$ centric slices of the image at each temporal sub-window of the temporal acquisition window are generated and summed to fill a 3D k-space volume. The radial (SOS) acquisition of the image is determined utilizing a customized rotation angle θ providing a uniform distribution of k-space spokes of the $k_z$ centric slices for each sub-window of the (taw).

12 Claims, 9 Drawing Sheets

(51) Int. Cl.
 *A61B 5/024* (2006.01)
 *G01R 33/48* (2006.01)
 *G01R 33/565* (2006.01)
 *G01R 33/563* (2006.01)
(52) U.S. Cl.
 CPC ... *G01R 33/4826* (2013.01); *G01R 33/56509* (2013.01); *G01R 33/5635* (2013.01); *G01R 33/56308* (2013.01)

(56) References Cited

FOREIGN PATENT DOCUMENTS

| KR | 10-1301490 B1 | 8/2013 |
| KR | 10-2014-0025267 A | 3/2014 |

* cited by examiner

Subject #1 RCA Root    Subject #3 RCA Distal End

MRI METHODS AND APPARATUS FOR FLEXIBLE VISUALIZATION OF ANY SUBSET OF AN ENLARGED TEMPORAL WINDOW

CLAIM OF PRIORITY

This application claims priority from U.S. provisional application 61/970,059 filed Mar. 25, 2014, the contents of which are incorporated by reference in its entirety.

BACKGROUND

1. Field of the Disclosure

The present disclosure relates to Magnetic Resonance Imaging (MRI) methods that provide imaging with reference to time. More particularly, the present disclosure relates to imaging with a flexible scan time during motion of a targeted organ.

2. Description of the Related Art

In general, a medical imaging device provides an image obtained from a patient. There are many types of medical imaging devices, such as ultrasonic diagnostic equipment, x-ray tomography equipment, magnetic resonance imaging equipment, and medical diagnostic equipment. In general, magnetic resonance imaging equipment functions provide superior contrast images of soft tissues of a human body, as well as provide various types of diagnostic information; thereby being a critical resource for diagnostic technology using medical images.

Generally, a magnetic resonance imaging device includes imaging equipment that diagnoses internal structures of a human body using the energy—already converted to a signal—induced from resonance reactions obtained by applying a constant rate of frequency and energy to nuclei of atoms of a patient while a predetermined magnetic field is applied to the patient.

There are unique challenges posed for providing high-resolution MRI when motion is involved. Such challenges are particularly present when, for example, performing an MRI of organs that have motion, such as coronary artery imaging, because of the complexities of both cardiac and respiratory motion.

Recent advances in both hardware and software MR technologies have permitted the performance of whole-heart imaging, specifically imaging for the visualization of the coronary arteries, so as to be performed in a clinically feasible scan time at both 1.5 T (tesla) and 3 T.

In practice, high-resolution imaging of a moving organ utilizes an ECG-gated k-space segmented acquisition strategy, which samples the 3D k-space volume only during the quiescent period of the motion of the organ such as the heart. For all of these known methods, a correctly timed trigger delay (TD) to synchronize the segmented k-space acquisition with the quiescent period of the cardiac cycle is essential.

Accordingly, a prior scout cine acquisition acquiring a series of images that are temporally spaced to acquire a series of images, is typically performed prior to the imaging to determine the optimal TD value for each individual, and subject who demonstrate heart-rate variability can present image quality degradation due to inaccurate TD timing errors.

An accurate timing determination for imaging can be difficult to ascertain in such subjects, as the heart rate can vary from beat to beat over the duration of a long scan duration, or change significantly in the presence or absence of breath-holding. In addition to the per-patient and physiological variability, the optimal period quiescent period with minimal motion for each artery branch may vary by anatomical position. Therefore, a single acquisition window may not necessarily be optimally timed for each coronary artery branch and region.

One way to attempt to overcome the aforementioned challenges is based on the incorporation of multiphase acquisition strategies with non-Cartesian sampling schemes into coronary imaging.

For example, a segmented 3D radial stack-of-stars acquisition approach generates four consecutive volumes at each temporal sub-window, and combines the sub-images to improve image quality.

Moreover, there have been studies exploring coronary acquisition over multiple temporal phases using k-space segmented strategies or high-resolution 3D cine approaches with radial or spiral sampling patterns. In all of the aforementioned multiphase 3D volumetric imaging approaches, the temporal window resolution is defined as the duration of each equally spaced temporal phase, and is not inherently designed for retrospective processing of any desired temporal subset within the acquisition window.

Accordingly, there remains a long-felt need in the art to provide a method that permits a retrospective processing of any desired temporal subset within the acquisition window.

SUMMARY

The present invention provides a novel acquisition scheme and apparatus configured to perform the acquisition scheme. According to the present invention, in which the reconstruction window can be selected retrospectively in an interactive manner by an operator, as any subset of the acquisition window of a predetermined minimum window size and a temporal resolution of a single readout.

For example, a method for controlling a magnetic resonance (MR) imaging system to provide retrospective reconstruction of an object image of a four-dimensional (4D) volume by an optimized rotation angle may include acquiring a temporal acquisition window based on an associated motion period of the object image, acquiring a plurality of image slices of the object, in which each $k_z$ plane is repeatedly determined during a sub-window of the temporal acquisition window; in response to a request, selecting a temporal acquisition sub-window for retrospective processing of the image slices to determine a period of minimal objection motion within the acquired temporal window.

The present invention also provides an acquisition strategy that enables a flexible reconstruction from any subset of the acquisition window. In a 3D stack-of-stars sequence acquired in an ECG-gated and k-space segmented scheme, a constant θ rotation is applied between each spoke, and this reconstruction holds true between the final radial spoke of the acquisition window and the first spoke in the subsequent heartbeat. Therefore, the acquired k-space distribution becomes sensitive to the number of projection lines, or the Turbo Field Echoes (nTFE) in each heart beat as the acquired radial spokes over multiple heartbeats are temporally indexed modulo of nTFE. Furthermore, to achieve flexible retrospective selection and reconstruction, any subset of this temporal window must have the sorted k-space spokes to be distributed as uniformly as possible for minimal artifacts.

In another aspect of the invention, a 3D stack-of-stars (SOS) sample scheme with golden-angle-derived interleaving can be used in conjunction with a dedicated visualization platform to allow interactive selection of any desired reconstruction window by the operator via a graphic user interface (GUI)-based graphic processing unit (GPU) accelerated reconstruction and visualization workflow to eliminate the drain on computer resources by performing rapid gridding to permit data to be displayed from any-operator select temporal subset.

In another aspect of the invention, the image reconstruction can be performed offline on the visualization platform.

In one particular aspect of the invention, the predetermined minimum window size is 30 milliseconds (ms) and the temporal resolution of a single readout is 4 ms. A radial stack-of-stars sampling is taken that is based on Golden Angle (GA) radial interleaving, which is processed retrospectively to determine the period of minimal coronary artery motion within the temporal window, which additional allows tailoring of the optimal reconstruction window to individual branches and regions of each coronary artery.

DETAILED DESCRIPTION

Hereinafter, aspects of the present invention will be described with reference to the accompanying drawings. In the following description, a detailed explanation of known related functions and constructions may be omitted to avoid unnecessarily obscuring an artisan's appreciation of the subject matter of the present invention with explanations of known functions. This invention may, however, be embodied in many different forms and should not be construed as limited to the exemplary embodiments set forth herein. The same reference numbers are used throughout the drawings to refer to the same or like parts.

Also, terms described herein, which are defined considering the functions of the present invention, may be implemented differently depending on the user and operator's intentions and practices. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily drawn to scale and certain features may be exaggerated or omitted in order to better illustrate and/or explain the present invention with better clarity.

(1) Rotation Angle Optimization for a K-Space Segmented 4D Radial Stack-of-Stars Acquisition In a first aspect of the invention, the Rotation Angle Optimization for a K-Space Segmented 4D radial stack-of-stars acquisition is a first example of how an enlarged temporal window permits the image generation. In this example, the radial stack-of-stars k-space approach typically utilizes radial sampling in the X, Y plane and Cartesian sampling in the Z plane.

Figure 1A:
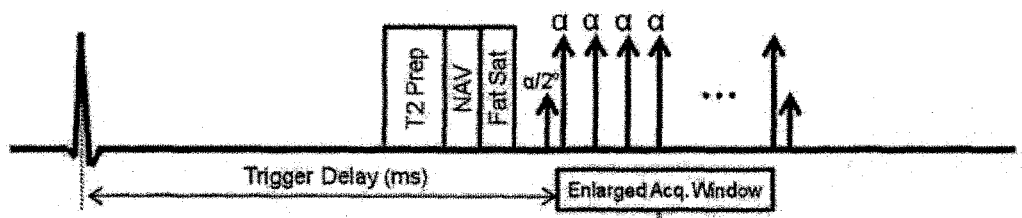
FIG. 1A shows the schematics of the proposed sampling scheme according to an aspect of the present invention.
Figure 1A:
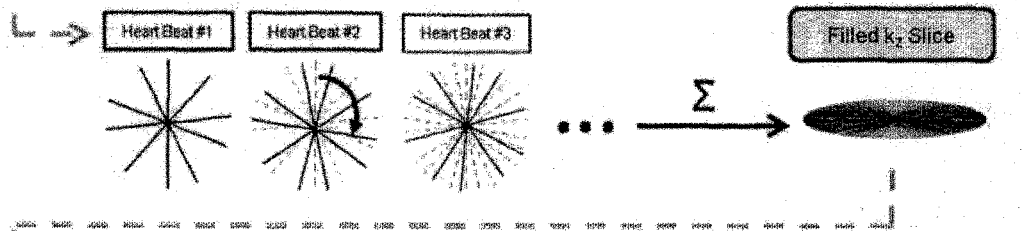
Figure 1A:
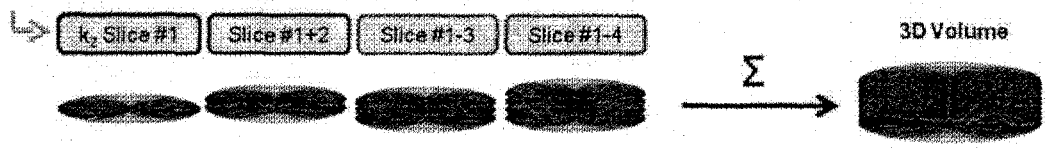

FIG. 1A shows a proposed sampling scheme. In this aspect of the invention, the proposed approach uses an ECG-gated, k-space segmented 3D balances steady-state free precession (b-SSFP) enlarged acquisition window that utilizes a radial stack-of-stars sampling strategy with a customized rotation angle $\theta$. Each $k_z$-plane is acquired preferably one at a time in a centric order, instead of all $k_z$ slices for a particular radial spoke position at once prior to applying a rotation angle.

Typically, for radial imaging strategies that yield a single volume, radial spokes are acquired in such way that that the resulting $k_z$ plane is uniformly distributed; thus, if n radial spokes are acquired on each plane, then a rotation angle that ensures uniform distribution satisfies the equation $\theta = j \cdot 180°/n$, where j is an integer such that a greatest common divisor (Gcd) (j, n)=1. $\theta$ is often set to $180°/n$, (i.e. j=1), where a sequential linear sweep is achieved through the plane.

Figure 1B:
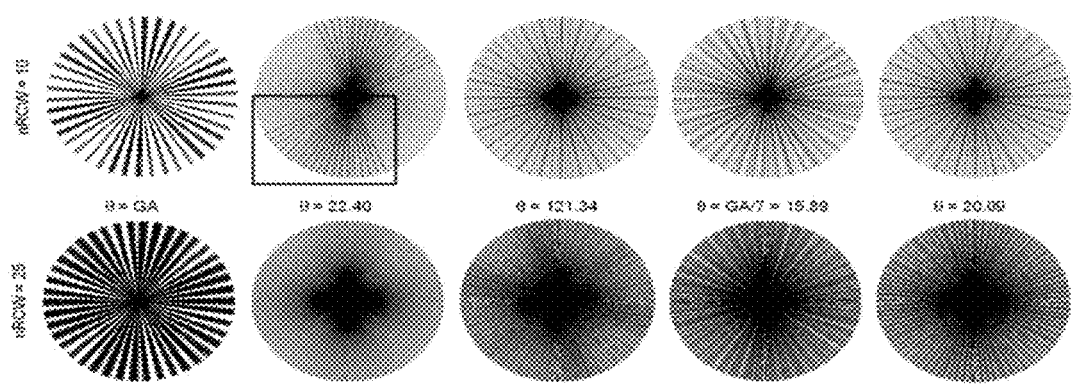
FIG. 1B depicts simulation results utilizing a 3D Stack-of-Stars Segmented Sequence and associated Optimal K-space Distribution according to according to a first aspect of the present invention.

FIG. 1B shows simulation results with nTR=48, nRHB=14. Top column shows the reconstruction with 25 consecutive TRs, bottom with 10. The leftmost column shows the k-space GA=111.246, where the spokes are clustered. Optimizing with $\lambda=0$ yielded $\theta=22.40$, which shows even distribution of the spokes at nRCW=25, but shows clustering in a sector at a smaller reconstruction window. The middle column optimized for the right term only, yielding $\theta=121.34$, where clustering in a sector was minimized. The final two columns were optimized using Eqn [1] with $\lambda=0.7$; showing $\theta=GA/7=15.89°$, and $\theta=20.09$, respectively.

Figure 1C:
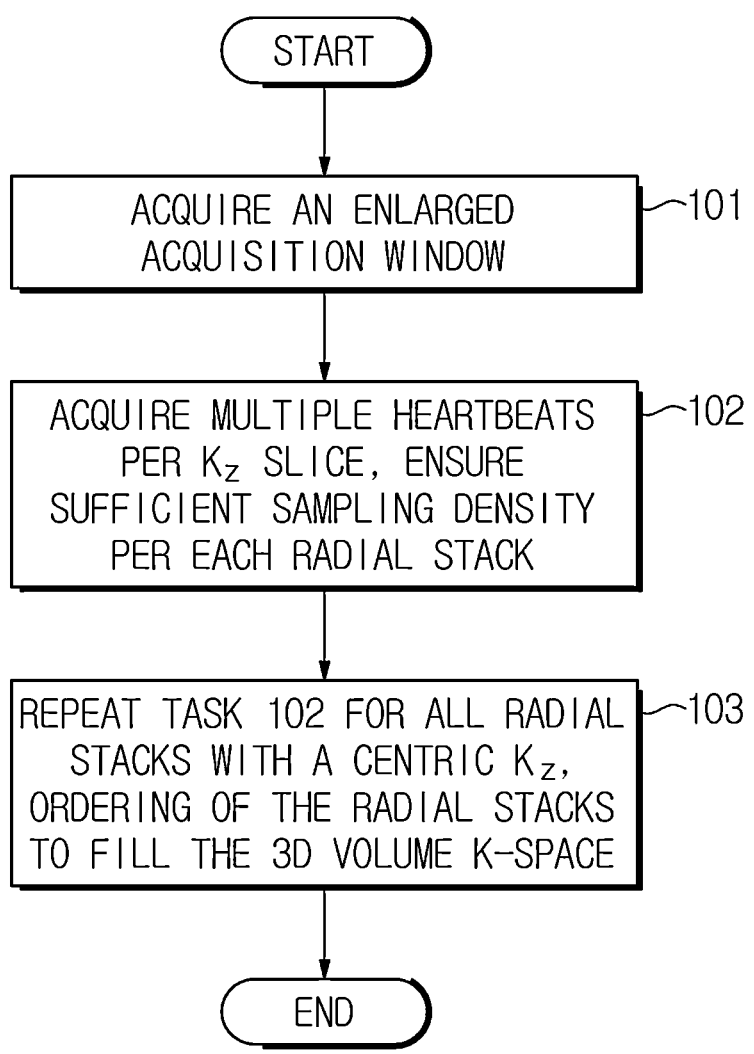
FIG. 1C is a flowchart that shows a general overview of obtaining the radial stack of stars according to an exemplary aspect of the invention.

FIG. 1C is a flowchart that shows a general overview of obtaining the radial stack of stars according to an exemplary aspect of the invention. At S101, there is an acquiring of an enlarged acquisition window. The enlarged acquisition window may be, for example, an acquisition window more than 80-120 ms duration (this is the current norm). The enlarged acquisition window is determined by the trigger delay and R-R interval of the patient. There is no set duration or look-up table to determine this. In the implemented example the inventors used 2 times the typical acquisition window size.

At task 102 multiple heart beats per $k_z$ slice are acquired, and to ensure that sufficient sampling density for each radial stack is performed.

At task 103 for each radial stack with a centric $k_z$, the task 102 is repeated so that there is an ordering of the radial stacks to fill the 3D volume k-space.

Figure 2:
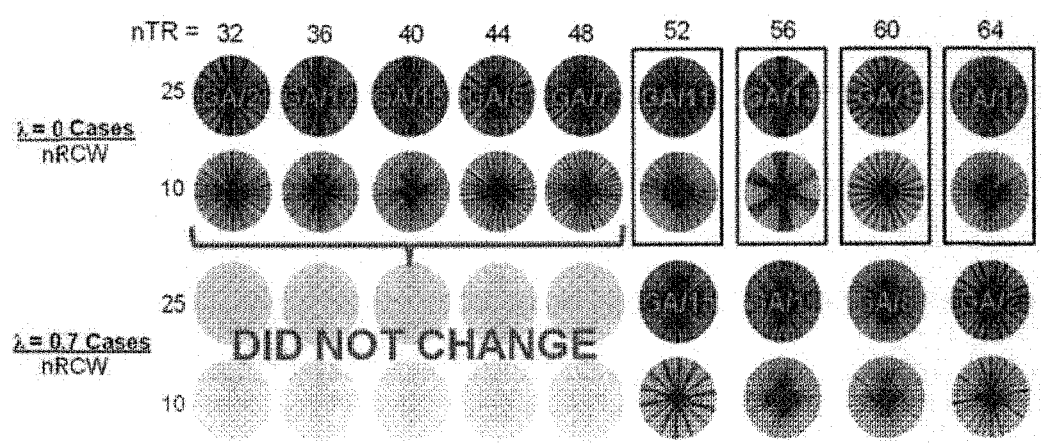
FIG. 2 depicts a set of optimal GA/n cases regarding the results associated with GA interleaving.

In order to achieve flexible retrospective selection and reconstruction, any subset of this temporal window should have the sorted k-space spokes to be distributed as uniformly as possible for minimal artifacts; and this distribution is not necessarily achieved by using $\theta=GA$ (Golden Angle), as shown in FIG. 2. An artisan should appreciate that in the present disclosure, the term "4D" refers to the X, Y and Z axes (3 dimensions) and time (the 4th dimension), so that motion can be reproduced, such as blood flow of a beating heart, by an MRI.

Referring to FIG. 2, the GA interleaving results in clustering of the spokes within a small temporal window when the acquisition window is set to 48 TFEs (left column) We also show that an improved distribution is feasible by using a different rotation angle (right column), and this hold true whether we use a reconstruction window of a single TR, or with 10 consecutive TRs, both containing spokes acquired over multiple repeated heartbeats (n=14). In the subsequent sections, we will show how this is achieved. The GA interleaving mentioned here is a standard radial acquisition where any 2 consecutive acquisitions have an angle increment of 111.2 deg. When we repeat the acquisitions during multiple heart beats, this GA increment rule leads to clustering. This in turn leads to streaking artifacts in images.

The optimal k-space distribution over any temporal window subset can be examined as a function of 4 parameters; the rotation angle θ between consecutive radial spokes, the number of projection lines per heart beat (nTFE), the number of heartbeats per $k_z$ slice (nHB), and the number of projections in each heartbeat used for reconstruction, i.e. the reconstruction window (nRCW).

An empirical simulation-based approach was developed to assess and optimize the radial coverage over a flexible subset of the temporal window. In this experiment, the repeated number of heartbeats was fixed to nRHB=14, as this value corresponded to a 100% Nyquist sampling density over an 80 ms temporal window. In this optimization, we seek an optimization to enforce both even spacing of the radial spokes over a flexible range of the reconstruction window (nRCW), and to minimize the clustering of spokes in any sector of the reconstruction window. Accordingly, we define the objective function to minimize the following:

$$C(nTFE, nHB) = \underset{\theta}{\operatorname{argmin}} \sum_{nRCW=Nmin}^{Nmax} \|\Delta\Theta_{\theta,nTFE}^{nHB,nRCW} - \Delta\theta_{Ll,nTFE}^{nHB,nRCW}\|_2^2 +$$

$$\lambda \cdot \max(|\Theta_{\theta,nTFE}^{nHB,nRCW} - \Theta_{Ll,nTFE}^{nHB,nRCW}|)$$

where $\Theta_{\theta,\ nTFE}^{nHR,\ nRCW}$ is a vector corresponding to the angles of the nHB·nRCW radial spokes acquired within the reconstruction window over multiple heartbeats when a θ rotation is used between subsequent spokes, $\Theta_{Ll,\ nTFE}^{nHB,\ nRCW}$ is the same vector of radial angles for the linear case with a 180°/(nHB·nRCW) rotation between subsequent spokes, and ΔΘ is the angle gap vector, which is the first differential of the Θ vector.

It should be noted that in this formulation, the reconstruction window is a subset of the acquisition window, hence nRCW≤nTFE. Additionally, $\Delta\Theta_{\theta,\ nTFE}^{nRHB,\ nRCW}$ is invariant to the reconstruction window position within the acquisition window, and its derivation is shown in the Appendix. For the final objective function determination, all range of nRCW values was accounted for by taking the summation of nRCW between Nmin and Nmax.

In this optimization, the first (left) term enforces uniform spacing, while the second (right) one minimizes clustering. We note the right term is not rotation invariant, thus the first element of angle of $\Theta_{\theta,\ nTFE}^{nHB,\ nRCW}$ was chosen such that the $\Theta_{\theta,\ nTFE}^{nHB,\ nRCW}$ was best aligned with $\Theta_{Ll,\ nTFE}^{nHB,\ nRCW}$, by minimizing $\|\Theta_{\theta,\ nTFE}^{nHB,\ nRCW} - \Theta_{Ll,\ nTFE}^{nHB,\ nRCW}\|_2^2$.

In this simulation, for each candidate θ at a fixed (nTFE, nHB) pair, the reconstruction window size nRCW was varied between Nmin=7 (98 spokes; 44% sampling density) and Nmax=25 (350 spokes; 156% sampling density), which corresponded to a temporal window of duration 32-115 ms at TR=4.6 ms. The λ value was empirically set to 0.7, which yielded the least clustering across all examined nTFEs.

In order to determine how well the GA/$n_{optimal}$ distributed the radial spokes among all possible input angles, an exhaustive numerical optimization using equation [1] was also performed. For this optimization, all θ values between [0.01, 179.99] were examined for the even nTFEs between 32 and 64 and nHB=14, and were sorted according to their corresponding cost values from the objective function. The θ=GA/$n_{optimal}$ was expressed as a percentile rank among all possible angles.

FIG. 2 shows the best GA/n cases where the top set was calculated using λ=0, and the bottom set using λ=0.7 to also penalize for clustering within a sector, which is successfully performed here.

Figure 3:
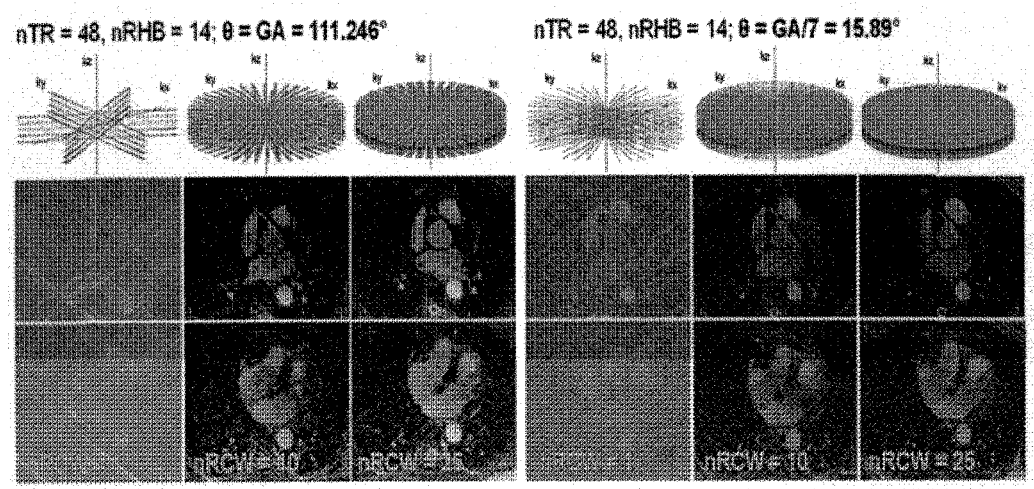
FIG. 3 depicts a whole-heart coronary MRI with an enlarged acquisition window according to the present invention.

FIG. 3 shows whole-heart coronary MRI acquired using θ=111.246 [GA] (left) and θ=15.89 [GA/7] (right). nRCW was varied between 1, 10 and 25.

Figure 4:
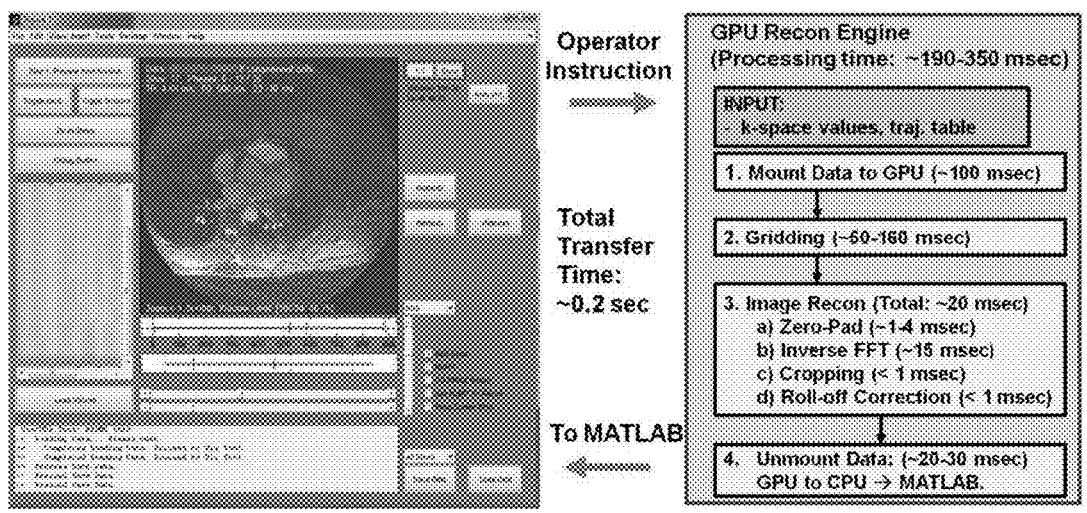
FIG. 4 depicts a Screenshot of GUI (left side) and workflow of GPU reconstruction, according to the present invention.

FIG. 4 shows screenshot of a GUI (left side) and a workflow of a GPU reconstruction engine (right side). Computation times are reported for each step, requiring a total of 190-350 milliseconds for the GPU operation to perform. An additional 0.2 ms is required for total latency to transfer the input and resulting image data back and forth between the GUI and GPU.

Figure 5:
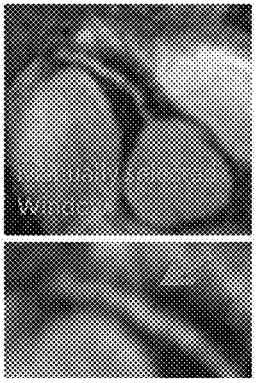
FIG. 5 depicts examples of manually selected and standard 120 ms reconstruction windows according to an aspect of the present invention.
Figure 5:
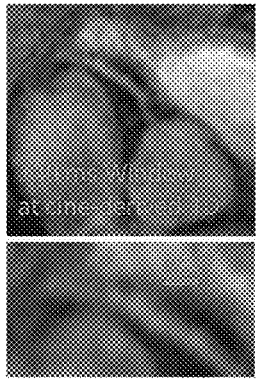
Figure 5:
Figure 5:

FIG. 5 shows Examples of the manually selected and the standard 120 ms reconstruction windows. In Subject #1's RCA root (left), the manually selected window mitigates the temporal blurring that can be in the standard window reconstruction. In Subject 3's RCA distal end (right), the distal branch of the RCA is fully recovered with this embodiment of the method according to the present invention.

Golden angle interleaving of radial k-space lines allows retrospective reconstruction of the data with different temporal resolution[1-4]. In coronary MRI with radial k-space sampling, data is usually acquired at the quiescent period to minimize the impact of cardiac motion. However, this timing is variable between subjects and also varies between different anatomical targets (e.g. right vs. left coronary arteries). Recently a segmented acquisition scheme where radial k-space data is acquired over a larger acquisition window was proposed to allow retrospective reconstruction of a subset of the data with minimal amount of cardiac motion. To enable reconstruction of a subset of radial k-space lines with minimal artifacts, uniform distribution of the radial lines becomes desirable. However, a reconstruction window may only partially cover the acquisition window, and such coverage is dependent on the pulse sequence parameters; thus, golden-angle interleaving over multiple segments does not necessarily result in a uniform distribution. In this way, an empirical approach is developed to determine the optimal rotation angle that evenly distributes the radial k-space spokes for any subset of the acquisition window in a 3D k-space segmented radial stack-of-stars coronary MRI.

In the proposed segmented radial stack-of-stars approach, each $k_z$-plane was sampled sequentially. The acquisition of each $k_z$-plane lasted multiple heartbeats, and the radial spokes in a given $k_z$-plane were rotated by an angle θ at each repetition time (TR). The k-space distribution is a function of 4 parameters: i) rotation angle between different radial spokes (θ); ii) the number of projection lines in each heart beat (nTR); iii) the number of heartbeats per $k_z$ plane (nHB); iv) the number of projections in each heartbeat used for reconstruction, i.e. the reconstruction window (nRCW). For this embodiment, we set nHB=14. To allow reconstruction for a flexible choice of nRCW, the goal is to enforce a uniform spacing of the radial spokes and to minimize the clustering of spokes in any area of the k-space, over a range of nRCW values. Accordingly, the objective function is defined in which we seek to minimize as follows:

$$C(nTR, nHB) = \arg\min_\theta \Sigma_{nRCW=N_{min}}^{N_{max}} \|\Delta\Theta_{\theta,\,nTR}^{nHB,\,nRCW} - \Delta\Theta_{Ll,\,nTR}^{nHB,\,nRCW}\|_2^2 + \lambda \cdot \max\left(|\Theta_{\theta,\,nTR}^{nHB,\,nRCW} - \Theta_{Ll,\,nTR}^{nHB,\,nRCW}|\right)$$

where $\Theta_{\theta,\,nTR}^{nHB,\,nRCW}$ is a vector corresponding to the angles of the nHB·nRCW radial spokes acquired within the reconstruction window over multiple heartbeats when a θ rotation is used between subsequent spokes, $\Theta_{Ll,\,nTR}^{nHB,\,nRCW}$ is the same vector of radial angles for the linear case with a 180°/(nHB·nRCW) rotation between subsequent spokes, and Δθ is the first derivative of θ. The first (left) term enforces uniform spacing, while the second (right) one minimizes clustering. We note the right term is not rotation invariant, thus the first element of angle of $\Theta_{\theta,\,nTR}^{nHB,\,nRCW}$ was chosen such that the $\Theta_{\theta,\,Ll,\,nTR}^{nHB,\,nRCW}$ was best aligned with $\Theta_{Ll,\,nTR}^{nHB,\,nRCW}$, by minimizing $\|\theta_{,\,nTR}^{nRHB,\,nRCW} - \Theta_{Ll,\,nTR}^{nRHB,\,nRCW}\|_2^2$. For numerical optimization of [1], θ was varied between 0.01 and 179.99° in step size of 0.01. Additionally, integer divisors of the GA (GA/1 thru GA/15) were additionally considered for θ.

With regard to results, FIG. 1B demonstrates the optimization for nTR=48 for two different reconstruction windows. The GA/n angle that yielded the minimal objective function yields a uniform distribution of the radial spokes. FIG. 2 shows the best GA/n reconstructions for nTRs between 32 and 64 (in step sizes of 4). There are four angle distributions (within boxes) that visually display clustering in the top set, for which λ=0. The bottom set shows the best GA/n terms when λ=0.7, where a different GA/n was selected for these 4 cases, while the remaining cases yielded the same GA/n as λ=0. FIG. 3 shows examples of coronary MR images acquired at nTR=48, nHB=14, and nRCW=1, 10 and 25, respectively; θ was varied between GA=111.246 and GA/7 (optimal GA/n case for nTR=48), showing less streaking artifacts when using the GA/7 scheme over the GA acquisition.

The proposed approach addresses the sub-optimal distribution of k-space spokes in a segmented radial stack-of-stars acquisition with different acquisition and reconstruction windows. Furthermore, the proposed optimization yields a rotation angle that provides an even distribution of spokes without clustering of spokes for a wide range of the reconstructed temporal window sizes, and can be used to generate the best GA/n angle approximation with good image quality over the typically used Golden Angle.

(2) Interactive Visualization of 4D Coronary MRI with Prolonged Acquisition Window: GPU-Accelerated Flexible Gridding Reconstruction for Lag-Free Performance Provides for Real-Time Workflow and Visualization of Non-Cartesian MR Data.

In another aspect of the invention, free-breathing 3D coronary MRI sequences are commonly acquired at the quiescent period of the cardiac cycle obtained from a prior breath-held scout CINE scan. However, the derived trigger delay timing may be inaccurate due to patient's R-R interval fluctuations between these scans, or due to breath-holding induced heart rate variability. Applicant proposes an approach that acquires a larger acquisition window and allows retrospective reconstruction of any desired temporal sub-window with minimal coronary motion [1]. This embodiment of the method uses a 3D stack-of-stars (SOS) sampling scheme with golden-angle-derived interleaving, and requires a dedicated visualization platform to allow interactive selection of any desired reconstruction window by the operator. However, 3D SOS reconstruction needs a computationally expensive gridding operation, which may bottleneck the visualization step by causing lagging performance that hinders the interactive clinical assessment. In this embodiment, we propose and evaluate a graphical user interface (GUI)-based, graphic processing unit (GPU)-accelerated reconstruction and visualization workflow. Our technique performs rapid gridding, and displays data from any operator-selected temporal subset of the time-sorted 4D k-space data in real-time to fit within a clinical workflow for coronary MR assessment.

With regard to proposed workflow, the acquired 3D radial SOS k-space data was processed using an in-house platform developed in MATLAB, and was integrated with GPU processing for rapid non-Cartesian gridding and real-time visualization. The raw k-space data is first indexed into the following coordinate system $[k_x, k_y, k_z, t]$, and passed to the GPU upon operator instruction. The provided GUI (FIG. 4) forwards all selected k-space points and coordinates from the selected slice and temporal window to the GPU reconstruction engine. The 2D image is then processed in the following steps: 1) The input parameters (namely the complex values and its coordinates) from MATLAB are mounted onto the GPU memory. 2) The gridding operation is parallelized and performed on a per-point basis, where gridded data from each GPU kernel is accumulated onto the final Cartesian grid using a dedicated GPU atomic addition operation [3,4]. 3) Image reconstruction is performed as a sequence of four sub-steps: a) zero-padding, b) inverse FFT, c) Cropping to the correct FOV, and 4) Roll-off correction. 4) The reconstructed image is mounted back to the CPU memory, and is returned to the MATLAB GUI.

With regard to experimental evaluation, All experiments were performed using coronary data acquired using a balanced SSFP sequence with radial SOS sampling, where the rotation angle was customized to account for uniform distribution over any subset within the acquisition window. For the GPU operation in this embodiment, a NVIDIA GeForce GTX 480 hardware was used, where all GPU operations were implemented using the CUDA platform. The performance of each GPU reconstruction substep was evaluated using different input k-space parameters typically acquired in high-resolution coronary MRI, and the measured times were averaged over 100 operations. For comparison, the reconstruction was also performed and evaluated using the NUFFT package [2] provided in MATLAB, which requires an initial preparation step that generates a look-up table.

Real-Time Visualization of Platform Design

An in-house accelerated reconstruction platform was developed in MATLAB for the visualization, and in C++ and NVIDIA CUDA for real-time non-Cartesian radial k-space gridding reconstruction. The raw k-space data and scanner parameters are used to automatically prepare the data for visualization on the platform, which consists of the following four steps: 1) temporal indexing and k-space look-up table generation, 2) coil compression, and 3) 3D volume data loading onto the CPU memory.

In step 1, the raw k-space data is first indexed into the following coordinate system $[k_x, k_y, k_z, t]$, and a look-up table is generated for rapid referencing of k-space from any desired temporal window. In step 2, a coil compression method proposed by Zhang et al. was employed to load the 3D k-space volume from 32 channels onto our standard workstation running the visualization platform; data was compressed from 32 to 8 compressed channels [32]. This compression method, which was originally proposed for Cartesian sampling, was feasible in our approach as the $k_z$-direction is fully sampled and thus was used as the spatially transformed direction to generate the hybrid k-space domain required for this approach. In step 3, the processed data is finally mounted onto the CPU memory for visualization. Mounted data is stored as temporally indexed and channel-compressed k-space values, and coordinate position.

The operator uses the GUI to select the slice and temporal window, and the developed GPU reconstruction engine performs the gridding operation of the selected non-Cartesian k-space data, and outputs the reconstructed image for immediate display onto the GUI panel. The gridding operation is parallelized and performed on a per-point basis, where gridded data from each GPU kernel is accumulated onto the final Cartesian grid using a dedicated GPU atomic addition operation [33]. Image reconstruction is performed as a sequence of four sub-steps: a) zero-padding, b) inverse FFT, c) Cropping to the correct FOV, and d) Roll-off correction. After completing these steps, the reconstructed image is mounted back to the CPU memory, and is returned to the MATLAB GUI.

For the GPU-gridding step, a fixed Kaiser-Bessel gridding kernel size of W=5.5 and a default oversampling factor of 1.25 were chosen in this embodiment, for which the corresponding gridding shape beta parameter set to 9.9981 per approximation method proposed by Beatty et al. [34].

The performance of each GPU reconstruction substep was evaluated using different input k-space parameters typically acquired in high-resolution coronary MRI, and the measured times were averaged over 100 operations. For comparison, the reconstruction was also performed and evaluated using the NUFFT package [35] provided in MATLAB, which requires an initial preparation step.

In Vivo Imaging

All scans were performed on a 1.5 T MR system using a 32-channel cardiac array under an institutional review board (IRB) approved protocol. Eight healthy subjects (5 male, mean age=37±18 years) were scanned. The ECG-gated 3D radial stack-of-stars SSFP coronary MRI was performed 2 minutes post-contrast injection (0.2 mmol/kg, Gadobenate Dimeglumine) with the following parameters: TR=4.6 ms, TE=1.8 ms, FA=100°, FOV=300×300×80–120 mm$^3$ Spatial resolution=1.3×1.3×2.0 mm$^3$. The subject-specific gating delay was determined from the a breath-held 2D cine, and was adjusted 50 ms prior to the determined quiescent period. The prolonged (i.e. enlarged) acquisition window size was set to 220 ms for nTFE=48 for subjects with a heart rate (HR)<65, while a smaller window of 166 ms (nTFE=36) was used for HR that exceeded 65. Accordingly, a custom radial angle of θ=15.89 (nTFE=48) and θ=9.27 (nTFE=36) was used (from Table 1), respectively. Accordingly the enlarged acquisition window in this case may range between 166 ms and 220 ms depending on the heart rate, wherein a typical acquisition window (not prolonged/enlarged) is about 30 ms at a minimum. The coronary MRI sequence used a T2Prep pulse with an echo time of 50 ms, a diaphragmatic navigator with a 7 mm gating window with slice-tracking (tracking factor=0.6), fat saturation, and a single half-alpha ramp up pulse, which was selected to minimize the time between all magnetization preparation pulses with volumetric imaging over the prolonged acquisition window to maximize the fat saturation over the enlarged acquisition window. Physiological parameters were extracted from the cine and the coronary imaging sequences. The optimal temporal reconstruction window for the right coronary artery (RCA) and the left anterior descending artery (LAD) were retrospectively determined manually by an experienced cardiologist using the developed visualization tool on a clinical workstation as follows: the standard 120 ms window at the TD was first examined; (120 ms Standard temporal window) the temporal window was then adjusted by the operator to yield improved visualization of the examined artery branch region. The window that yielded a notably better vessel region was then examined for its sharpness.

All image reconstruction was performed offline on the in-house visualization platform described previously. For assessment of the coronary vessel sharpness, 3D volumes were reconstructed to 0.65×0.65×1.0 mm$^3$ resolution with zero-filled interpolation using the platform. Vessel sharpness was measured using the SoapBubble Tool [36].

Results

Simulation of K-Space Distribution Optimization

FIG. 1B shows the best GA/n reconstructions for nTFEs between 32 and 64 (in step sizes of 4) when λ was set to 0.7; which was manually determined to provide a de-clustered selection of the spokes in all tested cases for all even nTFEs between 32 and 64.

Compared to other GA/n cases, these cases yielded both evenly distributed and de-clustered results after the proposed optimization. The look-up table was generated for all examined nTFEs=[32, 34, 36, . . . 64], and is reported in Table 1, along with the percentile rank out of 18000. These cases were within the top 12 percentile. A look-up-table-derived GA/n angle reported in Table 1 provided a reasonable coverage of the $k_x$-$k_y$ planes with good image quality even under undersampled conditions, as the proposed objective function employed in this embodiment accounts for both the optimal angle gap spacing and clustering of radial spokes within a sector of the $k_x$-$k_y$ plane. The reported rotation angles offer reasonable approximations for a range of nTFEs when nRHB is fixed to 14, and images were acquired using the reported table values for nTFE=36 and 48 in the subsequent sections.

Visualization Platform Evaluation

FIG. 4 shows the front-end GUI display developed for this software, and shows the block diagram of the reconstruction steps performed for an operator-selected temporal window, including the timing calculations for each reconstruction operation from the operator instructions to visualization. The total time required for the combined transfer of input and output data between MATLAB and GPU was constant at 0.18+0.01 seconds. Table 2 shows the average computation times at different reconstruction window sizes. The GPU implementation required a fixed 0.2 seconds for MATLAB-GPU interaction, 0.2-0.35 seconds for gridding—for a total of 0.4-0.55 seconds for visualization of the desired 2D high-resolution coronary MR image from the operator-specified temporal window and slice. For CPU gridding with NUFFT, an initial preparation step of the appropriate k-space look-up table took 1.5-10.5 seconds before performing the gridding and visualization steps in a single step (1.2-1.8 seconds), which required ~3 times than the GPU implementation.

Significant speed-up in total processing time is observed compared to the NUFFT-based preparation implemented in MATLAB, which required as much as 13 seconds (10.5 for prep+1.8 for gridding), and is therefore unsuitable for a flexible and retrospective reconstruction workflow for interactive visualization.

In Vivo Imaging

All scans were completed successfully. The average navigator efficiency for the whole-heart coronary imaging across the seven subjects was 41±11%. Table 3 reports the adjusted temporal window and its normalized vessel sharpness score, as well as its difference between the score from the standard window FIG. 3 demonstrates examples of motion corrected vessel at the root of the RCA, and a distal RCA vessel recovered by the operator using the proposed approach.

FIG. 4 shows operator's workflow to optimize the visualization at the mid-RCA region by manipulating the reconstruction temporal in an interactive manner. In this case, the operator was able to fully recover the RCA that was non-descript with the initial window (left) by gradually adjusting the reconstruction window to that yielding optimal visualization with minimal blurring motion. Out of 30 examined artery regions, 5 were fully visualized using the proposed method when it was non-descript for the standard window (e.g. FIG. 5-2, right), and 9 were sufficiently well-visualized using the standard window. Two were not examined due to any visible artery region throughout the entire acquisition window, while one mid-RCA branch was not measured due to a sharp bend that prevented the reformatting step necessary for sharpness assessment. For the RCA root and LAD, the average sharpness scores were (manually selected vs standard 120 ms windows): RCA (Root) 0.40±0.06 vs 0.38±0.07; (LAD) 0.36±0.06 vs 0.34±0.07.

In this embodiment, Applicants have demonstrated the feasibility of acquiring an enlarged acquisition window using a 3D radial stack-of-stars sampling scheme with a GA-derived customized angle for optimal k-space distribution to enable reconstruction of any flexible temporal subset of the acquisition window in a retrospective manner, allowing tailored reconstruction for different coronary artery branches and regions within the acquired 3D volume. An optimized rotation angle for the 3D k-space segmented sequence was derive from the GA radial sampling trajectory, allowing a flexible reconstruction with a minimal subset of at least 7 k-space spokes per heart-beat and a temporal resolution of 32 ms. A simulation was performed to report the optimal rotation angle for a fixed nTFE and nHB pair. A look-up-table was derived for the optimal GA/n angle as reported in Table 1, which provides a reasonable coverage of the $k_x$-$k_y$ planes with good image quality even under undersampled conditions accounting for both the optimal angle gap spacing and clustering of radial spokes within a sector of the $k_x$-$k_y$ plane. For rapid and interactive visualization of the data, a GPU-based reconstruction engine was combined with the GUI developed in MATLAB to enable an interactive assessment. When compared with the MATLAB-based NUFFT reconstruction method that is employed for offline non-Cartesian methods, the GPU-based radial reconstruction requires no dedicated preparation, and is therefore more suitable for on-the-fly visualization within 1 second even under computationally heavy conditions, which matches previously reported ranges [37]. While the gridding reconstruction using the NUFFT package in MATLAB performs sufficiently well for most offline radial gridding reconstructions at our site that are acquired with lower spatial resolutions, a more robust GPU gridding implementation enabled the real-time visualization approach required for the clinical assessment tool in this embodiment.

The strength of the proposed combined acquisition and reconstruction approach lies in its ability to enable visualization of any 2D slice of the whole-heart 3D volume in real-time from the time-sorted k-space data. The additional consideration of the temporal dimension in the reconstruction step enables a retrospective examination of any flexible subset of the enlarged acquisition window. Further scan time reduction can be gained by undersampling the radial stack-of-stars sequence by incorporating iterative reconstruction approaches such as parallel imaging or compressed sensing.

The present invention has additional aspects within its spirit and scope in addition to the aforementioned disclosures. First, the contrast mechanism throughout the enlarged acquisition window in the examples discussed above was not optimized with respect to: a) fat suppression, and b) contrast optimization throughout the enlarged acquisition window. For fat suppression, a conventional fat saturation preparation can be employed prior to the radial SSFP acquisition of the enlarged acquisition window. Thus, this aspect of the invention could be adversely affected by fat signal recovery, and thus was subsequently used with contrast enhancement. A combination with fat water separation methods, such as Dixon techniques, or using water selective imaging approaches, such as ATR or wideband SSFP, can potentially address this at the expense of prolonged scan time. Post-contrast injection imaging is used in these examples for the improvement in the visualization of the coronary arteries due to the shortened T1 relaxation values.

In conclusion, a whole-heart coronary imaging approach with an enlarged acquisition window by which the trigger delay and acquisition window can be adjusted interactively to tailor the reconstruction of different coronary branch regions. The sub-optimal distribution of k-space spokes in a segmented radial stack-of-stars acquisition with different acquisition and reconstruction windows is first addressed by the proposed optimization approach, and a GUI tool is developed to enable a flexible GPU-based offline radial k-space reconstruction for interactive assessment of any desired temporal window from the 4D coronary k-space data.

With regard to results, FIG. 4 shows the timing of each of the reconstruction operation from the operator instructions to visualization. The total time for the combined transfer between MATLAB and GPU was 0.2 seconds. Table 1 shows the average computation times at different reconstruction window sizes. The GPU implementation required a fixed 0.2 seconds for MATLAB-GPU interaction, 0.2-0.35 seconds for gridding—for a total of 0.4-0.6 seconds for visualization of the desired 2D image from any desired temporal window and slice. For CPU gridding with NUFFT, an initial preparation step of the appropriate k-space lookup table took 1.5-10.5 seconds before performing the gridding and visualization steps in a single step (1.2-1.8 seconds), which required ~3 times than the GPU implementation.

Significant speed-up in total processing time is observed compared to the NUFFT-based preparation. When the GPU-based gridding parameters were matched to the default input parameters for NUFFT-based gridding (kernel shape parameter W from 5.5 to 6.0 and oversampling factor from 1.25 to 2.0), the average computation time using the GPU increased from 0.53 sec to 0.86 sec; significantly less than the equivalent NUFFT-based gridding step that may take as much as 13 seconds (10.5 for prep+1.8 for gridding), which is unsuitable for a flexible and retrospective reconstruction workflow for interactive visualization.

Therefore, a GUI tool that provides flexible GPU-based offline radial k-space reconstruction is developed, and enables on-the-fly assessment of any desired temporal window to retrospectively select a motion-free 3D volume from the 4D coronary k-space data.

TABLE 1

Average Processing Times GPU vs CPU Methods Test Methodology Total

| Test Methodology | Total Computation Time (seconds) | | | | |
|---|---|---|---|---|---|
| (#Samples × #Spokes × #Coils) #k-space points to grid | GPU-TRANSFER | GPU-GRID | GPU-TOTAL | CPU-PREP | CPU-GRID/TOTAL |
| 1.3 mm resolution Recon | | | | | |
| RecWin Size = 7; (464 × 98 × 8) = 363776 pts | 0.18 ± 0.01 | 0.19 ± 0.02 | 0.37 ± 0.04 | 1.5 ± 0.1 | 1.2 ± 0.1 |
| RecWin Size = 16; (464 × 224 × 8) = 831488 pts | 0.18 ± 0.01 | 0.23 ± 0.02 | 0.41 ± 0.04 | 3.5 ± 0.4 | 1.4 ± 0.1 |
| RecWin Size = 48; (464 × 672 × 8) = 2494464 pts | 0.18 ± 0.01 | 0.35 ± 0.03 | 0.53 ± 0.04 | 10.5 ± 1.1 | 1.8 ± 0.2 |
| Submillimeter resolution Recon | | | | | |
| RecWin Size = 48; (600 × 864 × 8) = 4147200 pts | 0.19 ± 0.01 | 0.78 ± 0.08 | 0.96 ± 0.10 | 17.9 ± 1.8 | 2.8 ± 0.29 |

(3) 4D Whole-Heart Coronary MRI with an Enlarged Acquisition Window to Address Inaccurate Trigger Delay Timing Errors Derived from Scout Cine-SSFP In another aspect of the invention, High-resolution 3D coronary MRI requires a correctly timed trigger delay (TD) to synchronize the segmented k-space acquisition with the quiescent period of the cardiac cycle. While a scout cine-CMR is used to manually assess this trigger delay, heart-rate changes change between the breath-held cine and the free-breathing 3D volumetric acquisition may result in inaccurate TD timing1,2. Additionally, left and right coronaries may have different quiescent periods. In this work, we present a whole-heart coronary acquisition method to address inaccurate trigger delay timings by performing k-space sampling over an enlarged acquisition window that spans more than the quiescent period derived from the scout cine scan.

Accordingly, seven healthy subjects (5 male, 38±19 years) were scanned using a radial stack-of-stars approach with an enlarged acquisition window[2,3]. All scans were performed on a 1.5 T MR system using a 32-channel cardiac array. The ECG-gated 3D radial stack-of-stars SSFP coronary MRI was performed 2 minutes post-contrast injection (0.2 mmol/kg, MultiHance) with the following parameters: TR=4.6 ms, TE=1.8 ms, FA=100o, FOV=300×300×90–110 mm³. Spatial resolution=1.3×1.3×2.0 mm³. The subject-specific TD was determined from the initial breath-held 2D cine at the beginning of the imaging protocol, and its trigger delay was adjusted to begin 50 ms prior to the determined quiescent period from the scout scan. The prolonged acquisition window was set to either 36 TRs (166 ms), or 48 TRs (221 ms) depending on the subject's observed heart rate. The coronary MRI sequence was prepared by a T2Prep pulse (50 ms), a diaphragmatic navigator with a 7 mm gating window with slice-tracking, fat saturation, and a half-alpha ramp up. Physiological parameters were extracted from the cine-SSFP and the coronary imaging sequences. All images were retrospectively reconstructed offline, where the optimal temporal reconstruction window for the right coronary artery (RCA) and the left anterior descending artery (LAD) were determined manually as follows: the standard 120 ms window at the TD was first examined; the temporal window was then adjusted by the operator to yield improved visualization of the examined artery branch region. The window that yielded a notably better vessel region was then examined for its sharpness.

With regard to results, all scans were completed successfully. The average navigator efficiency for the whole-heart coronary imaging across the seven subjects was 41±11%, and the average imaging time was 16±4 minutes as no accelerated imaging methods was used. Table 1 summarizes the physiological parameters, including the initial heart rate recorded by the scanner operator during scan setup, the R-R interval extracted from the initial reference Cine-CMR, as well as the whole-heart sequence, the adjusted temporal window and its normalized vessel sharpness score, as well as its difference between the score from the standard window.

Across all seven subjects, there was an average offset of 50±20 ms between the average R-R intervals of the initial cine-SSFP and the WH coronary MRI protocols. FIG. 5 demonstrates examples of motion corrected vessel at the root of the RCA, and a distal RCA vessel recovered by the operator using the proposed approach. Out of 28 examined artery regions, 4 were fully visualized using the proposed method when it was non-descript for the standard window (e.g. FIG. 5, right), and 6 were sufficiently well visualized using the standard window. 4 were not examined due to any visible artery region throughout the entire acquisition window, while one mid-RCA branch was not measured due to a sharp bend that prevented the reformatting step necessary for sharpness assessment. For the RCA root and LAD, the average sharpness scores were (manually selected vs standard 120 ms windows): RCA (Root) 0.38±0.05 vs 0.35±0.04; (LAD) 0.35±0.06 vs 0.33±0.06.

The results of the table herein below demonstrates that a whole-heart coronary MRI approach with an enlarged acquisition window to address trigger delay errors according to the present invention provides improvement in the utilization of MRI on moving objects heretofore unknown.

HR (BPM) and R-R Interval (ms)
Recon Window Position and Vessel Sharpness Scoring

| Subj. | Ref HR | R-R (Ref. Cine) (avg, [min, max]) | R-R (WH Coronary) (avg ± std, [min, max]) | RCA (Root) | RCA (Mid) | RCA (Distal) | LAD |
|---|---|---|---|---|---|---|---|
| | | | | [TD offset (ms), Recon Window Size (ms)]; Sharpness Score (Diff with Standard Recon) | | | |
| 1 | 63 | 820 [650, 1] | 780 ± 50 [670, 970] | [−37, 87], 0.43 (+0.06) | [−41, 51], 0.36 (*) | [−28, 78], 0.22 (*) | [−9, 106], 0.30 (+0.01) |
| 2 | 67 | 870 [340, 1120] | 920 ± 30 [700, 1010] | [0, 120], 0.37 (S) | [−0.45, 64], 0.41 (+0.05) | [−37, 74], 0.29 (+0.05) | [0, 120], 0.30 (S) |
| 3 | 80 | 740 [660, 820] | 670 ± 40 [340, 800] | [−13, 83], 0.39 (+0.05) | [−18, 64], 0.37 (*) | [−41, 74], **0.31 (*)** | [−37, 87], 0.40 (+0.11) |

HR (BPM) and R-R Interval (ms)
Recon Window Position and Vessel Sharpness Scoring

| Subj. | Ref HR | R-R (Ref. Cine) (avg, [min, max]) | R-R (WH Coronary) (avg ± std, [min, max]) | RCA (Root) | RCA (Mid) | RCA (Distal) | LAD |
|---|---|---|---|---|---|---|---|
| | | | | [TD offset (ms), Recon Window Size (ms)]; Sharpness Score (Diff with Standard Recon) | | | |
| 4 | 68 | 870 [770, 990] | 890 ± 40 [770, 990] | [−41, 120], 0.39 (+0.02) | [−41, 120], 0.31 (+0.00) | ND | [+9, 106], 0.39 (−0.02) |
| 5 | 66 | 820 [780, 880] | 770 ± 50 [650, 850] | [−22, 97], 0.39 (+0.04) | GEOM | [−5, 87], 0.29 (+0.08) | [0, 120], 0.27 (S) |
| 6 | 68 | 910 [796, 1050] | 870 ± 30 [730, 970] | [0, 120], 0.42 (S) | [−14, 92], 0.49 (+0.03) | [0, 120], 0.29 (S) | [0, 120], 0.41 (S) |
| 7 | 49 | 1210 [900, 1420] | 1120 ± 90 [850, 1330] | [0, 120], 0.28 (S) | ND | ND | ND |

(*) - Vessel was non-descript with the standard, but visualized with the manually window.
(S) - The standard window yielded good image quality after visual assessment.
BOLD - reconstructions are shown in FIG. 1.
GEOM - curvature in artery prevented reformatting for measurement.
ND - vessel was non-descript.

Hereinafter, a basic exemplary layout of an MRI apparatus is discussed herein below that is configured to perform the aforementioned methods according to the present invention.

Figure 6:
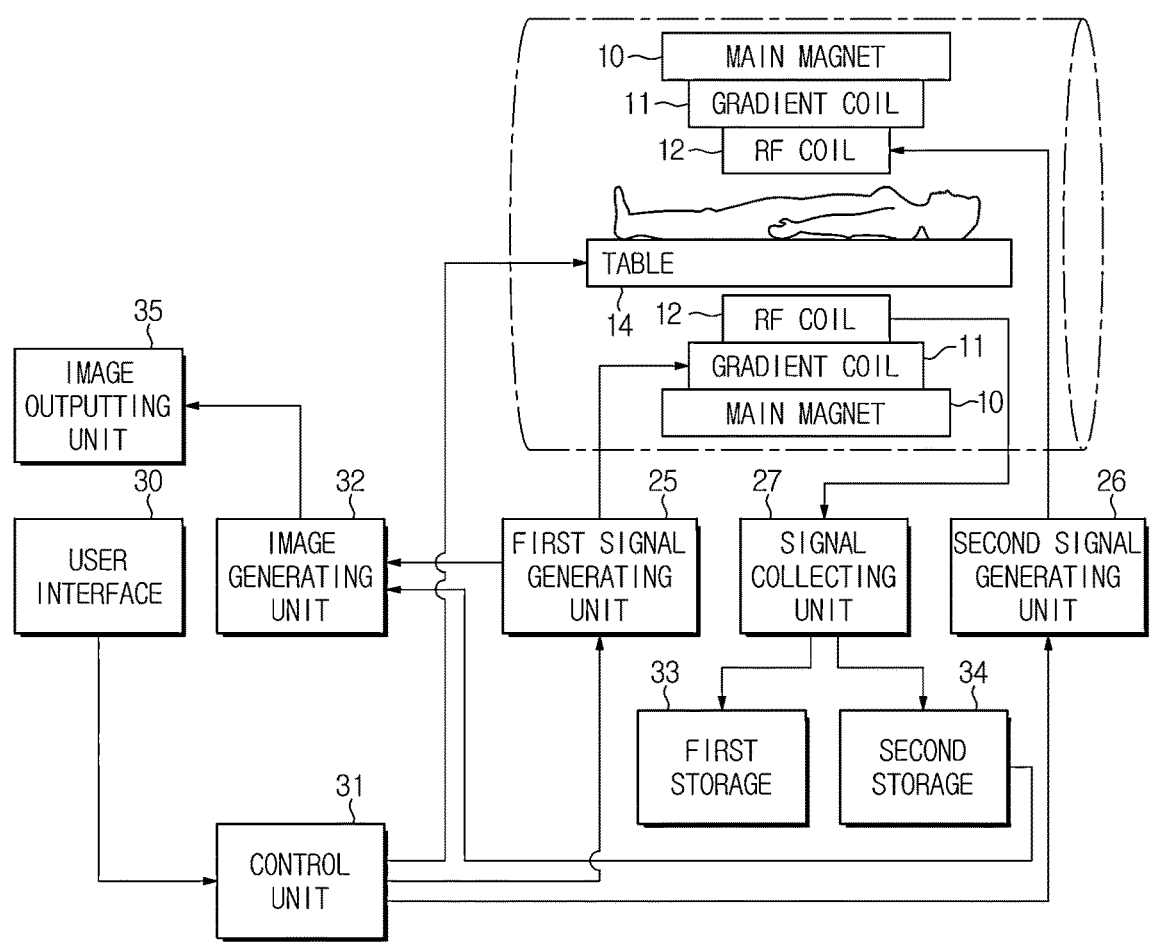
FIG. 6 shows an example of an MRI apparatus according to the present invention.

FIG. 6 is a view illustrating a structure of a magnetic resonance imaging (MRI) apparatus or system according to an exemplary embodiment of the present invention, for generating or reconstructing images from MRI data. It is to be understood that this is only an example of one way the hardware may be structured, and that the claimed invention is not limited to the example depicted herein.

Referring now to FIG. 6, the MRI apparatus typically includes a main magnet 1, a gradient coil 11, a radio frequency (RF) coil 12, a shield 1, a table 14, a first signal generating unit 25, a second signal generating unit 26, a signal collecting unit 27, a user interface 30, a control unit 31, an image generating unit 32, a first storage 33, a second storage 34, and an image outputting unit 35.

The main magnet 10, the gradient coil 11, and the RF coil 12 are elements for generating a magnetic field to induce magnetic resonance signals from atomic nuclei inside a human body, and may be implemented as a magnet, coils, etc. The shield 13 blocks an electromagnetic wave generated by the RF coil 12 from being radiated to the outside. A target object, for example, a patient, lies on the table 14 inside the shield 13, and the table 14 may move by control of the control unit 31 in or out of the assembly of components 10-13, to position the patient for MRI photography.

The first signal generating unit 25, the second signal generating unit 26, and the signal collecting unit 27 are components for transmitting signals to generate the magnetic field in the gradient coil 11 and the RF coil 12 by the control of the control unit 31, or for collecting signals received in the RF coil 12 and providing the image generating unit 32 with the collected signals, and may be implemented as an oscillator, an amplifier, a modulator, a demodulator, an analog-to-digital converter (ADC), a digital-to-analog converter (DAC), etc. The user interface 30, the control unit 31, the image generating unit 32, the first storage 33, the second storage 34, and the image outputting unit 35 are components for controlling the first signal generating unit 25 and the second signal generating unit 25, or for processing signals collected by the signal collecting unit 27, and may be implemented as a computer and peripheral devices of the computer.

The main magnet 10 generates a static magnetic field for arranging directions of magnetic dipole moments of atomic nuclei, typically hydrogen nuclei in water molecules, inside the human body in one direction. Examples of the main magnet 10 for generating the static magnetic field include a permanent magnet, a room temperature electromagnet, a superconductivity electromagnet, etc. A magnetic field generated by the superconductivity electromagnet is strong and uniform, and thus the superconductivity electromagnet is mainly used as the main magnet 10. For example, if hydrogen atomic nuclei inside the human body are placed in the static magnetic field generated by the main magnet 10, directions of magnetic dipole moments of the hydrogen atomic nuclei are arranged in a direction of the static magnetic field generated by the main magnet 10 in order to go into a lower energy state. To maintain a thermal parallel state, the number of atomic nuclei in a low energy state is actually slightly greater than the number of atomic nuclei in a high energy state. In this regard, an energy difference between atomic nuclei in different energy states is proportional to an intensity of the static magnetic field generated by the main magnet 10, and has an intrinsic Larmor frequency associated with Larmor precession of the atomic nuclei. For example, if the intensity of the static magnetic field generated by the main magnet 10 is 1 Tesla, the Larmor frequency of a hydrogen atomic nucleus in the static magnetic field generated by the main magnet 10 is 42.58 MHz, and the Larmor frequency of a sodium atomic nucleus therein is 11.27 MHz.

The gradient coil 11 generates a gradient magnetic field that varies at a constant gradient with respect to each of a plurality of directions, for example, directions x, y, and z, in proportion to a distance from a reference location within the static magnetic field generated by the main magnet 10. In this regard, the reference location may be an origin point of a 3D coordinate system when a space including a static magnetic field generated by the main magnet 10 is presented as the 3D coordinate system. Each of the magnetic resonance signals received by the RF coil 12 has location information in a 3D space due to the gradient magnetic field generated by the gradient coil 11. The gradient coil 11 may comprise an X gradient coil for generating the gradient magnetic field that varies in the direction x, a Y gradient coil for generating the gradient magnetic field that varies in the direction y, and a Z gradient coil for generating the gradient magnetic field that varies in the direction z.

The RF coil 12 generates an electromagnetic wave signal having an RF corresponding to a type of an atomic nucleus, i.e., an RF signal, and applies the electromagnetic wave signal to the target object in order to transit the atomic nucleus from the low energy state to the high energy state.

Atomic nuclei inside the target object are excited by the applied electromagnetic wave signal. In this regard, the target object is generally an MR image captured site of the human body, or may be a living body other than the human body or an inanimate object.

For example, the RF coil 12 may generate the electromagnetic wave of 42.58 MHz to transit an energy state of the hydrogen atomic nucleus within the static magnetic field of 1 Tesla. Also, the RF coil 12 may generate the electromagnetic wave of 11.27 MHz to transit an energy state of the sodium atomic nucleus within the static magnetic field of 1 Tesla. If the electromagnetic wave signal generated by the RF coil 12 is applied to an atomic nucleus, the atomic nucleus is transited from a low energy state to a high energy state. Thereafter, if the electromagnetic wave signal generated by the RF coil 13 disappears, i.e. if the electromagnetic wave applied to the atomic nucleus disappears, the atomic nucleus radiates an electromagnetic wave having the same Larmor frequency while being transited from the high energy state to the low energy state.

The RF coil 12 receives an electromagnetic wave signal radiated from atomic nuclei inside the target object. The electromagnetic wave signal is referred to as a free induction decay (FID) signal. The FID signal is referred to as an echo signal with respect to the electromagnetic wave signal applied to the target object as a magnetic resonance signal used to generate a magnetic resonance image. A length of a time interval from a time point when the electromagnetic wave signal is applied to the target object, i.e. a time point when the electromagnetic wave signal is generated, to a time point when the electromagnetic wave signal is received from the target object is referred to as an echo time (TE). A length of a time interval when an application of the electromagnetic wave signal to the human body repeats is referred to as a repetition time (TR).

The RF coil 12 may be implemented as one coil having a function of generating an electromagnetic wave having an RF corresponding to a type of an atomic nucleus and a function of receiving an electromagnetic wave radiated from the atomic nucleus, or may be implemented as a transmission coil having the function of generating the electromagnetic wave having the RF corresponding to the type of the atomic nucleus and a reception coil having the function of receiving the electromagnetic wave radiated from the atomic nucleus. In particular, according to the present embodiment of FIG. 6, the reception coil of the RF coil 12 may be implemented as a dual tuned coil capable of receiving several frequencies in one coil, may be implemented as a multi-channel coil capable of simultaneously receiving a plurality of magnetic resonance signals, or may be implemented as a dual tuned multi-channel coil.

The user interface 30, which includes circuitry such as sensors, processors and microprocessors configured for operation, receives a command from an operator of the MRI apparatus of FIG. 6 and outputs the command to the control unit 31. The user interface 30 may be implemented as a general input device of a computer, such as a keyboard and a mouse. The image outputting unit 35 which includes circuitry such as sensors, processors and microprocessors configured for operation, and display that is preferably a thin film technology (TFT) but is not limited thereto, outputs the magnetic resonance image generated by the image generating unit 32. The image generation unit 32 which includes circuitry such as sensor, processors and microprocessors configured for operation, may preferably contain a graphics processing unit (GPU) that is configured for operation to perform the methods described herein above, and while in the above examples in the specification a NVIDIA GeForce GTX 480 hardware was used, where all GPU operations were implemented using the CUDA platform, the invention is not limited thereto, as other hardware can be configured that equivalents or successors of the hardware discussed herein, as various types of hardware may be used for image reconstruction. The image outputting unit 35 may be implemented as a general output device of the computer such as a monitor. The control unit 31, which includes circuitry such as a processor or microprocessor configured for operation, controls the first signal generating unit 25, the second signal generating unit 26, the signal collecting unit 27, and the image generating unit 32 according to the command output from the user interface 30. The image generating unit 32 generates a magnetic resonance image by using magnetic resonance signals that are collected by the signal collecting unit 27 and are stored in the first storage 33 and the second storage 34. The control unit 31 and the image generating unit 32 may be implemented as a high performance special purpose computer capable of promptly processing a large amount of data required to generate the magnetic resonance image. Meanwhile, it will be understood by one of ordinary skill in the art that the terms "generating the magnetic resonance image" may be replaced by various terms such as "reconstructing the magnetic resonance image".

The control unit 31, which as discussed before includes circuitry such as processors and microprocessors configured for operation, generates a control signal indicating an alternating signal having a frequency varying at a certain gradient with respect to each of the directions x, y, and z, and outputs the control signal to the second signal generating unit 26. The first signal generating unit 25 generates the alternating signal having a frequency varying at a constant gradient with respect to each of the directions x, y, and z according to the control signal received from the control unit 31, and outputs the alternating signal to the gradient coil 11. The gradient coil 11 generates a gradient magnetic field that varies at a constant gradient with respect to each of the directions x, y, and z according to the alternating signal received from the first signal generating unit 26. The control unit 31 generates a control signal indicating a pulse train, and outputs the control signal to the second signal generating unit 26. The second signal generating unit 26 generates an alternating signal having the pulse train according to the control signal received from the control unit 31, and outputs the alternating signal to the RF coil 12. The RF coil 12 generates an electromagnetic wave signal having the pulse train according to the alternating signal received from the second signal generating unit 26. The first signal generating unit 25 and the second signal generating unit 26 may be implemented as ADCs for converting analog signals received from the control unit 31 into digital signals, oscillators for generating source signals, modulators for modulating the source signals according to signals received from the control unit 31, amplifiers for amplifying the signals modulated by the modulators, etc. Such amplified signals are sent to the coils 11, 12.

The first signal collecting unit 25 collects magnetic resonance signals induced by atomic nuclei through the RF coil 12. The first signal collecting unit 25 may be implemented as an amplifier for amplifying magnetic resonance signals received from the RF coil 12, a demodulator for demodulating the magnetic resonance signals amplified by the amplifier, a DAC for converting analog magnetic resonance signals demodulated by the demodulator into digital magnetic resonance signals, etc. The magnetic resonance signals converted into digital form are separately stored as acquired MRI data in the first non-transitory storage 33 and the second non-transitory storage 34. The first storage 33 and the second storage 34 are not necessarily physically separated storages but are spaces for separately storing different types of magnetic resonance signals. For example, the first storage 33 and the second storage 34 may be different storage regions of a hard disk. Alternatively, the first storage 33 and the second storage 34 may be combined and implemented by a single storage unit.

The RF coil 12 generates an electromagnetic wave from an alternating current applied from the second signal generating unit 26 to the RF coil 12, and receives an electromagnetic wave by a collection of signals by the signal collecting unit 27, and thus it is possible to freely adjust a time when the RF coil 12 generates a pulse and a time when the RF coil 12 receives the pulse.

In a preferred embodiment shown in FIG. 6, the image generating unit 32 performs the method for generating or reconstructing images from the acquired MRI data with image enhancement according to selected enlarged acquisition windows and temporal reconstruction windows as described herein.

Figure 7:
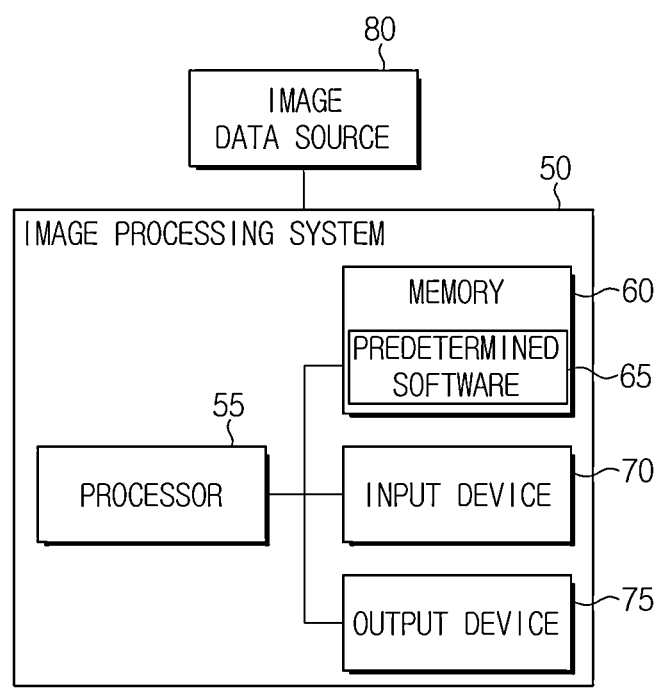
FIG. 7 shows an exemplary embodiment of an image processing system according to the present invention.

In an alternative exemplary embodiment of the present invention, as shown in FIG. 7, the apparatus performs the method for generating or reconstructing images from the MRI data with may include an image processing system 50 having a processor 55, a non-transitory memory for storing data and machine executable code including operational programs such as predetermined software 65, an input device 70, and an output device 75. The output device 75 may include the image outputting unit 35 of FIG. 6, which may be a display, a printer, etc. for displaying reconstructed MR images, or the output device 75 may be a communications interface for connecting to the image outputting unit. The input device 70 may include a keyboard, touchscreen and/or a mouse for receiving user inputs and selections, and may incorporate or be connected to the user interface 30 of FIG. 6. In addition, the input device 70 and the output device 75 may operate together as a graphic user interface (GUI), for example, provided to the user of the MRI apparatus by the user interface 30 in a manner known in the art. In alternative embodiments, the input device 70 and the output device 75 may include a touch screen to provide the GUI which responds to user touches, in a manner known in the art, for operating the image processing system of the present invention.

In the alternative exemplary embodiment, the image processing system 50 is a stand-alone specialized computer, and the image reconstruction may be performed off-line; that is, independent of the image acquisition process of, for example, the MRI system of FIG. 6. Alternatively, the image reconstruction may be performed contemporaneously with the acquisition of images of a subject by the MRI system of FIG. 6.

The image reconstruction is performed using customized software, and such predetermined software 65 may be generated using mathematical software development and authoring tools, such as MATLAB, a mathematical and numerical computing environment implemented as a software application commercially available from MATHWORKS, Natick, Mass., U.S.A. Alternatively, the predetermined software may be implemented by any known programming language or environment, for example, by using the C++ programming language. However, the claimed invention is not limited to these items.

The image processing system 50 receives and processes image data from an image data source 80 with the received image data stored in the memory. The image data source 80 may include the MRI apparatus of FIG. 6, which may be implemented using, for example, a 1.5 T magnet as the main magnet 10, commercially available. In an alternative exemplary embodiment, the image data source 80 is operatively connected by a wired and/or wireless connection to the image processing system. The image data source 80 may also be embodied as one or both of the first storage 33 and the second storage 34 in FIG. 6 for receiving and storing data corresponding to RF signals, MR signals, and other known data signals from the respective coils 11, 12.

In further alternative embodiments, the image processing system 50 is connected, using a wired and/or wireless connection, to a computer network, such as the Internet, and receives the image data from at least one or even multiple remote sources, such as medical image data archives as the image data source. For example, the MRI images collected by a hospital or other MRI facilities, for example, using the apparatus of FIG. 6 or other known MRI apparatus, may store the images in a storage facility as the image data source, can be remotely accessed by the image processing system of the present invention using known communication devices and methods.

The above-described methods according to the present invention can be implemented in hardware, firmware or as software or computer code that is stored on a non-transitory machine readable medium such as a CD ROM, a RAM, thumbnail drive, a floppy disk, a hard disk, or a magneto-optical disk or computer code downloaded over a network originally stored on a remote recording medium or a non-transitory machine readable medium and stored on a local non-transitory recording medium, so that the methods described herein are loaded into hardware such as a general purpose computer, or a special processor or in programmable or dedicated hardware, such as an ASIC or FPGA. As would be understood in the art, all of the computer, the processor, microprocessor, controller, or the programmable hardware contain circuitry that is typically integrated, and can include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "controller", "processor" or "microprocessor" constitute hardware in the claimed invention. Under the broadest reasonable interpretation, the appended claims constitute statutory subject matter in compliance with 35 U.S.C. §101 and none of the elements constitute of software per se.

The terms "unit" or "module" as may be used herein is to be understood as constituting or operating in conjunction with hardware such as a circuit, integrated circuit, processor, controller, or microprocessor configured for a certain desired functionality in accordance with statutory subject matter under 35 U.S.C. §101, and such terms do not constitute software per se.

Any of the functions and steps provided in the Figures may be implemented in hardware, software or a combination of both and may be performed in whole or in part within the programmed instructions of a special computer. No claim element herein is to be construed under the provisions of 35 U.S.C. 112, sixth paragraph, unless the element is expressly recited using the phrase "means for".

We claim:

1. A method for controlling a magnetic resonance (MR) imaging system to provide retrospective reconstruction of an object image of a four-dimensional (4D) volume by an optimized rotation angle, the method comprising:
generating a magnetic field around an object by a main magnet and a gradient magnetic coil;
receiving a signal from the object by a radio frequency coil;
acquiring a temporal acquisition window based on an associated motion period of the object image,
acquiring a plurality of image slices of the object, in which each $k_z$ plane is repeatedly determined during a sub-window of the temporal acquisition window, wherein the plurality of image slices of the object are acquired based at least in part on the signal;
in response to a request, selecting a temporal acquisition sub-window for retrospective processing of the image slices to determine a period of minimal objection motion within the acquired temporal window;
wherein the rotation angle is optimized for a segmented 4D radial stack-of-stars acquisition during the temporal acquisition window by:
acquiring radial stacks of the image of the object by performing a radial stack-of-stars acquisition to determine a plurality of $k_z$ plane samples of the object, in which each $k_z$ plane is repeatedly determined during the sub-window of the temporal acquisition window;
generating a plurality of consecutive volumes of $k_z$ centric slices of the image at each temporal sub-window of the temporal acquisition window that are summed to fill a 3D k-space volume; and
displaying an image based at least in part on displaying the reconstructed object image based at least in part on the period of minimal objection motion;
wherein the radial stack-of-stars (SOS) acquisition of the image is determined utilizing a customized rotation angle θ to provide a uniform distribution of k-space spokes of the $k_z$ centric slices of the image for each sub-window of the temporal acquisition window.

2. The method according to claim 1, wherein the $k_z$ plane samples of the $k_z$ centric slices of the image are acquired by performing Cartesian sampling of the object in a Z plane and radial sampling of the object in an X, Y plane.

3. The method according to claim 1, comprising performing radial sampling of the object by two planes and performing Cartesian sampling of the object by a third plane.

4. The method according to claim 1, wherein each sub-window of the temporal acquisition window is determined utilizing Golden Angle (GA) interleaving to determine the customized rotation angle θ for radial spoke rotation.

5. The method according to claim 1, wherein the temporal acquisition window is enlarged according to a quantity of multiple heart beats per $k_z$ slice.

6. The method according to claim 1, wherein an optimal k-space distribution over any temporal acquisition sub-window is determined as a function of:
a rotation angle θ between consecutive radial spokes, a number of projection lines per heart beat (nTFE), a number of heart beats per $k_z$ slice (nHB), and a number of projections in each heart beat used for reconstruction.

7. The method according to claim 1, wherein the temporal acquisition window is a sum of a plurality of temporal acquisition sub-windows.

8. The method according to claim 6, wherein the optimal k-space distribution comprises:

$$C(nTFE, nHB) = \mathrm{argmin}_\theta \sum_{nRCW=Nmin}^{Nmax} \|\Delta\Theta^{nHB,nRCW}_{\theta,nTFE} - \Delta\Theta^{nHB,nRCW}_{LI,nTFE}\|_2^2 +$$
$$\lambda \cdot \max(|\Theta^{nHB,nRCW}_{\theta,nTFE} - \Theta^{nHB,nRCW}_{LI,nTFE}|)$$

where $\Theta_{\theta,\,nTFE}^{nHB,\,nRCW}$ a vector corresponding to the angles of the nHB·nRCW radial spokes acquired within s reconstruction window over multiple heartbeats when a θ rotation is used between subsequent spokes, $\Theta_{LI,\,nTFE}^{nHB,\,nRCW}$ is a same vector of radial angles for a linear case with a 180°/(nHB·nRCW) rotation between subsequent spokes, and ΔΘ is an angle gap vector, which is a first differential of a Θ vector.

9. The method according to claim 1, wherein the reconstruction is a subset of the temporal acquisition window in which nRCW≤nTFE in which nTFE comprises a number of projection lines per heartbeat, and nRCW is a number of projections in each heartbeat in reconstruction window.

10. The method according to claim 8, wherein $\Delta\Theta_{\theta,\,nTFE}^{nRHB,\,nRCW}$ is invariant to a reconstruction window position within the temporal acquisition window.

11. The method according to claim 2, wherein in the SOS acquisition is configured for enforcing uniform spacing and minimizing a clustering of spokes of a radial slice in accordance with following:

$$C(nTR, nHB) = \mathrm{argmin}_\theta \sum_{nRCW=Nmin}^{Nmax} \|\Delta\Theta^{nHB,nRCW}_{\theta,nTR} - \Delta\Theta^{nHB,nRCW}_{LI,nTR}\|_2^2 +$$
$$\lambda \cdot \max(|\Theta^{nHB,nRCW}_{\theta,nTR} - \Theta^{nHB,nRCW}_{LI,nTR}|),$$

wherein $\Theta_{\theta,\,nTR}^{nHB,\,nRCW}$ comprises a vector corresponding to angles of a number of heart beats per $k_z$ slice x number of projections in each heartbeat used for reconstruction (reconstruction window RCW) in which nHB·nRCW radial spokes acquired within the reconstruction window over multiple heartbeats when a 0 rotation is used between subsequent spokes, $\Theta_{LI,\,nTR}^{nHB,\,nRCW}$ is a same vector of radial angles for a linear case with a 180°/(nHB·nRCW) rotation between subsequent spokes, and ΔΘ is a first derivative of Θ, wherein a first left term enforces uniform spacing, while a second right term minimizes clustering.

12. The method according to claim 10, wherein a GA/n angle yielding a minimal objective function comprises the minimal objective function yielding a uniform distribution of radial spokes.

* * * * *

UNITED STATES PATENT AND TRADEMARK OFFICE
CERTIFICATE OF CORRECTION

PATENT NO. : 9,702,956 B2  
APPLICATION NO. : 14/274065  
DATED : July 11, 2017  
INVENTOR(S) : Keigo Kawaji et al.

Page 1 of 1

It is certified that error appears in the above-identified patent and that said Letters Patent is hereby corrected as shown below:

In the Claims

Column 22, Claim 8, Line 16 should read as follows:  
--...is a vector corresponding to the...--

Column 22, Claim 8, Line 18 should read as follows:  
--...a reconstruction window over...--

Column 22, Claim 11, Lines 49-50 should read as follows:  
--...heartbeats when a θ rotation...--

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*